US009656009B2

(12) United States Patent
Kheradvar et al.

(10) Patent No.: US 9,656,009 B2
(45) Date of Patent: May 23, 2017

(54) CARDIAC ASSIST SYSTEM USING HELICAL ARRANGEMENT OF CONTRACTILE BANDS AND HELICALLY-TWISTING CARDIAC ASSIST DEVICE

(75) Inventors: Arash Kheradvar, Blythewood, SC (US); Morteza Gharib, San Marino, CA (US); Anna Grosberg, Cambridge, MA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 1067 days.

(21) Appl. No.: 12/218,237

(22) Filed: Jul. 11, 2008

(65) Prior Publication Data

US 2009/0131740 A1 May 21, 2009

Related U.S. Application Data (60) Provisional application No. 60/959,297, filed on Jul. 11, 2007, provisional application No. 61/010,786, filed on Jan. 11, 2008.

(51) Int. Cl.
*A61N 1/362* (2006.01)
*A61M 1/10* (2006.01)
(Continued)

(52) U.S. Cl.
CPC ........ *A61M 1/1068* (2013.01); *A61M 1/1003* (2014.02); *A61M 1/1048* (2014.02);
(Continued)

(58) Field of Classification Search
CPC ............ A61F 2/2481; A61F 2002/2478; A61F 2002/2481; A61F 2002/915; A61F 2/2478;
(Continued)

(56) References Cited

U.S. PATENT DOCUMENTS 2,434,835 A   1/1948   Colley
2,663,467 A   12/1953  Douglass et al.
(Continued)

FOREIGN PATENT DOCUMENTS

WO   WO 92/06738   4/1992
WO   WO 02/28450   4/2002
(Continued)

OTHER PUBLICATIONS

Notification of Transmittal of the International Search Report and the Written Opinionof the International Searching Authority.
(Continued)

*Primary Examiner* — Lindsey G Wehrheim
(74) *Attorney, Agent, or Firm* — One LLP (57) ABSTRACT

A cardiac assist system using a helical arrangement of contractile bands and a helically-twisting cardiac assist device are disclosed. One embodiment discloses a cardiac assist system comprising at least one contractile elastic band helically arrangement around a periphery of a patient's heart, where upon an actuation the band contracts helically, thereby squeezing the heart and assisting the pumping function of the heart. Another embodiment discloses a helically twisting cardiac-apex assist device comprising an open, inverted, substantially conical chamber with two rotatable ring portions of different diameters located at the base and apex of the chamber, with a plurality of substantially helical connecting elements positioned substantially flush with the chamber wall and connecting the two rotatable ring portions, whereby a relative twisting motion of the two rings causes a change in volume of the chamber thereby assisting the cardiac pumping function.

16 Claims, 5 Drawing Sheets

(51) Int. Cl.
*A61M 1/12* (2006.01)
*A61N 1/365* (2006.01)
*A61F 2/24* (2006.01)
*A61F 2/915* (2013.01)
*A61N 1/36* (2006.01)
*A61M 1/36* (2006.01)

(52) U.S. Cl.
CPC ............ *A61M 1/122* (2014.02); *A61F 2/2478* (2013.01); *A61F 2/2481* (2013.01); *A61F 2/915* (2013.01); *A61M 1/36* (2013.01); *A61N 1/36* (2013.01); *A61N 1/3627* (2013.01); *A61N 1/36514* (2013.01); *A61N 1/36521* (2013.01)

(58) Field of Classification Search
CPC ... A61F 2/915; A61N 1/3627; A61N 1/36521; A61N 1/36514; A61N 1/36; A61M 1/36; A61M 1/1068; A61M 1/1003; A61M 1/1048; A61M 1/122
USPC .................................................. 600/17; 607/3
See application file for complete search history.

(56) References Cited

U.S. PATENT DOCUMENTS

| | | |
|---|---|---|
| 2,961,213 A | 11/1960 | Philippovic |
| 3,066,853 A | 12/1962 | Landenberger |
| 3,371,906 A | 3/1968 | Lubold |
| 3,504,550 A | 4/1970 | Koch et al. |
| 3,511,583 A | 5/1970 | Brown |
| 3,593,718 A | 7/1971 | Krasner et al. |
| 3,602,105 A | 8/1971 | Slusher |
| 3,638,536 A | 2/1972 | Kleinwachter et al. |
| 3,677,667 A | 7/1972 | Morrison |
| 3,730,186 A | 5/1973 | Edmunds et al. |
| 3,756,243 A | 9/1973 | Schulte |
| 3,768,931 A | 10/1973 | Willis, Jr. |
| 3,982,722 A | 9/1976 | Bernard |
| 4,092,010 A | 5/1978 | Carlson, Jr. |
| 4,240,434 A | 12/1980 | Newkirk |
| 4,256,094 A | 3/1981 | Kapp et al. |
| 4,292,969 A | 10/1981 | Raible et al. |
| 4,401,107 A | 8/1983 | Haber et al. |
| 4,463,502 A | 8/1984 | Fitzgerald et al. |
| 4,553,271 A | 11/1985 | Baker |
| 4,602,911 A | 7/1986 | Ahmadi et al. |
| 4,697,989 A | 10/1987 | Perlov et al. |
| 4,705,518 A | 11/1987 | Baker et al. |
| 4,721,030 A | 1/1988 | Paynter |
| 4,794,912 A | 1/1989 | Lia |
| 4,808,079 A | 2/1989 | Crowley et al. |
| 4,915,017 A | 4/1990 | Perlov |
| 4,917,579 A | 4/1990 | Torma |
| 5,019,121 A | 5/1991 | Krauter |
| 5,033,270 A | 7/1991 | Hardt |
| 5,166,563 A | 11/1992 | Bassine |
| 5,197,984 A | 3/1993 | Kedem |
| 5,203,172 A | 4/1993 | Simpson et al. |
| 5,344,385 A | 9/1994 | Buck et al. |
| 5,394,132 A | 2/1995 | Poil |
| 5,443,504 A | 8/1995 | Hill |
| 5,549,619 A | 8/1996 | Peters et al. |
| 5,562,595 A | 10/1996 | Neisz |
| 5,637,083 A | 6/1997 | Bertrand et al. |
| 5,653,676 A | 8/1997 | Buck et al. |
| 5,658,237 A | 8/1997 | Francischelli |
| 5,678,564 A | 10/1997 | Lawrence et al. |
| 5,697,884 A | 12/1997 | Francischelli et al. |
| 5,697,952 A | 12/1997 | Francischelli et al. |
| 5,701,919 A | 12/1997 | Buck et al. |
| 5,716,379 A | 2/1998 | Bourgeois et al. |
| 5,800,528 A | 9/1998 | Lederman et al. |
| 5,984,857 A | 11/1999 | Buck et al. |
| 5,996,964 A | 12/1999 | Ben-Shalom |
| 6,053,210 A | 4/2000 | Chapman et al. |
| 6,074,179 A | 6/2000 | Jokela et al. |
| 6,076,013 A | 6/2000 | Brennan et al. |
| 6,146,114 A | 11/2000 | Nardacci et al. |
| 6,151,525 A | 11/2000 | Soykan et al. |
| 6,210,432 B1 * | 4/2001 | Solem .............. A61B 17/00234 623/1.11 |
| 6,224,540 B1 | 5/2001 | Lederman et al. |
| 6,254,355 B1 | 7/2001 | Gharib |
| 6,270,053 B1 | 8/2001 | Eshel |
| 6,278,847 B1 | 8/2001 | Gharib et al. |
| 6,314,322 B1 | 11/2001 | Rosenberg |
| 6,331,188 B1 | 12/2001 | Lau et al. |
| 6,343,605 B1 | 2/2002 | Lafontaine |
| 6,352,553 B1 | 3/2002 | Van Der Burg et al. |
| 6,352,561 B1 | 3/2002 | Leopold et al. |
| 6,361,637 B2 | 3/2002 | Martin et al. |
| 6,395,016 B1 | 5/2002 | Oron et al. |
| 6,408,878 B2 | 6/2002 | Unger et al. |
| 6,425,856 B1 * | 7/2002 | Shapland .............. A61F 2/2481 600/16 |
| 6,428,464 B1 | 8/2002 | Bolling |
| 6,450,942 B1 | 9/2002 | Lapanashvili et al. |
| 6,464,476 B2 | 10/2002 | Ross et al. |
| 6,506,025 B1 | 1/2003 | Gharib |
| 6,508,756 B1 | 1/2003 | Kung et al. |
| 6,517,570 B1 | 2/2003 | Lau et al. |
| 6,520,986 B2 | 2/2003 | Martin et al. |
| 6,551,350 B1 | 4/2003 | Thornton et al. |
| 6,580,503 B2 | 6/2003 | Gharib et al. |
| 6,582,208 B2 | 6/2003 | Gharib |
| 6,607,368 B1 | 8/2003 | Ross et al. |
| 6,608,668 B2 | 8/2003 | Gharib et al. |
| 6,613,072 B2 | 9/2003 | Lau et al. |
| 6,620,095 B2 | 9/2003 | Taheri |
| 6,654,102 B1 | 11/2003 | Modares et al. |
| 6,670,699 B2 | 12/2003 | Mikubo et al. |
| 6,671,558 B1 | 12/2003 | Soykan et al. |
| 6,672,847 B2 | 1/2004 | Dooley |
| 6,679,687 B2 | 1/2004 | Gharib |
| 6,713,944 B2 | 3/2004 | Omata et al. |
| 6,716,002 B2 | 4/2004 | Higashino |
| 6,717,172 B2 | 4/2004 | Gharib et al. |
| 6,720,710 B1 | 4/2004 | Wenzel et al. |
| 6,787,972 B2 | 9/2004 | Kim et al. |
| 6,866,842 B1 | 3/2005 | Chancellor et al. |
| 6,884,040 B2 | 4/2005 | Dooley |
| 6,902,545 B2 | 6/2005 | Bertolero et al. |
| 6,910,466 B2 | 6/2005 | Veinotte |
| 6,956,230 B1 | 10/2005 | Gharib et al. |
| 6,984,201 B2 | 1/2006 | Khaghani et al. |
| 7,006,132 B2 | 2/2006 | Pereira et al. |
| 7,021,604 B1 | 4/2006 | Werner et al. |
| 7,031,775 B2 | 4/2006 | Soykan et al. |
| 7,033,132 B2 | 4/2006 | Gharib |
| 7,048,519 B2 | 5/2006 | Fong et al. |
| 7,051,738 B2 | 5/2006 | Oron et al. |
| 7,094,040 B2 | 8/2006 | Higashino et al. |
| 7,104,313 B2 | 9/2006 | Pokharna et al. |
| 7,107,777 B2 | 9/2006 | Vaiyapuri et al. |
| 7,118,525 B2 * | 10/2006 | Coleman et al. ............... 600/16 |
| 7,155,288 B2 | 12/2006 | Soykan et al. |
| 7,163,385 B2 | 1/2007 | Gharib et al. |
| 7,331,991 B2 | 2/2008 | Kheradvar et al. |
| 7,387,500 B2 | 6/2008 | Gharib |
| 7,398,818 B2 | 7/2008 | Gharib et al. |
| 7,491,170 B2 | 2/2009 | Gharib |
| 7,524,298 B2 | 4/2009 | Gharib et al. |
| 7,612,869 B2 | 11/2009 | Pereira et al. |
| 7,749,152 B2 | 7/2010 | Gharib et al. |
| 2002/0082469 A1 | 6/2002 | Taheri |
| 2003/0121644 A1 | 7/2003 | Tonosaki et al. |
| 2003/0152469 A1 | 8/2003 | Dante et al. |
| 2003/0164231 A1 | 9/2003 | Goodson et al. |
| 2003/0209006 A1 | 11/2003 | Gharib et al. |
| 2003/0233023 A1 | 12/2003 | Khaghani et al. |
| 2003/0233143 A1 | 12/2003 | Gharib et al. |
| 2003/0234595 A1 | 12/2003 | Takahashi et al. |
| 2003/0235504 A1 | 12/2003 | Lemoff et al. |

(56) References Cited

U.S. PATENT DOCUMENTS

| | | |
|---|---|---|
| 2004/0013536 A1 | 1/2004 | Hower et al. |
| 2004/0018100 A1 | 1/2004 | Takagi et al. |
| 2004/0031594 A1 | 2/2004 | Vaiyapuri et al. |
| 2004/0037035 A1 | 2/2004 | Ohashi et al. |
| 2004/0048778 A1 | 3/2004 | Druggan |
| 2004/0097787 A1* | 5/2004 | French .................. A61F 2/2481 600/37 |
| 2004/0133260 A1 | 7/2004 | Schwartz et al. |
| 2004/0143319 A1 | 7/2004 | Schwartz et al. |
| 2004/0151607 A1 | 8/2004 | Gharib |
| 2004/0152945 A1 | 8/2004 | Kantrowitz et al. |
| 2004/0171904 A1 | 9/2004 | French et al. |
| 2004/0184237 A1 | 9/2004 | Chang |
| 2004/0225177 A1 | 11/2004 | Coleman et al. |
| 2005/0008509 A1 | 1/2005 | Chang |
| 2005/0070755 A1 | 3/2005 | Zheng |
| 2005/0092944 A1 | 5/2005 | Patterson |
| 2005/0098299 A1 | 5/2005 | Goodson et al. |
| 2005/0187620 A1* | 8/2005 | Pai et al. ..................... 623/2.37 |
| 2005/0197527 A1 | 9/2005 | Bolling |
| 2005/0231914 A1 | 10/2005 | Mikubo et al. |
| 2005/0265978 A1 | 12/2005 | Chancellor et al. |
| 2005/0275494 A1 | 12/2005 | Gharib et al. |
| 2005/0277865 A1 | 12/2005 | Gharib et al. |
| 2006/0008450 A1 | 1/2006 | Verfaillie et al. |
| 2006/0084835 A1 | 4/2006 | Laufer |
| 2006/0106449 A1 | 5/2006 | Ben Muvhar |
| 2006/0120048 A1 | 6/2006 | Houle et al. |
| 2006/0131003 A1 | 6/2006 | Chang et al. |
| 2006/0139882 A1 | 6/2006 | Mikubo et al. |
| 2006/0147487 A1 | 7/2006 | Henderson |
| 2006/0216173 A1* | 9/2006 | Kheradvar et al. ........... 417/478 |
| 2006/0217588 A1 | 9/2006 | Gross et al. |
| 2007/0185371 A1 | 8/2007 | Bortolotti |
| 2008/0077070 A1 | 3/2008 | Kopia |
| 2008/0097497 A1 | 4/2008 | Assad et al. |
| 2008/0194905 A1 | 8/2008 | Walsh |
| 2008/0260705 A1 | 10/2008 | Marban et al. |
| 2009/0007923 A1 | 1/2009 | Dancu |
| 2009/0088651 A1 | 4/2009 | Shuros et al. |
| 2009/0105631 A1 | 4/2009 | Kieval |
| 2009/0177270 A1 | 7/2009 | Agnew et al. |
| 2009/0281560 A1 | 11/2009 | Wexner et al. |
| 2010/0114299 A1 | 5/2010 | Ben Muvhar et al. |

FOREIGN PATENT DOCUMENTS

| | | |
|---|---|---|
| WO | WO 2005/011502 A2 | 12/2005 |
| WO | PCT/US2005/018455 | 4/2006 |
| WO | PCT/US2005/018455 | 11/2006 |
| WO | PCT/US2005/018592 | 12/2006 |
| WO | PCT/US2005/047234 | 2/2007 |
| WO | PCT/US2005/047234 | 7/2007 |
| WO | PCT/US2006/000986 | 9/2007 |
| WO | PCT/US2007/000309 | 11/2007 |
| WO | PCT/US2007/000309 | 7/2008 |
| WO | PCT/US2008/008539 | 6/2009 |
| WO | PCT/US2008/008539 | 1/2010 |
| WO | PCT/US2011/059597 | 6/2012 |
| WO | PCT/US2011/059597 | 5/2014 |

OTHER PUBLICATIONS

Helm, P., et al., "Measuring and Mapping cardiac fiber and laminar architecture using diffusion tensor MR imaging," Ann NY Acad Sci, 2005, 1047(1), pp. 296-307.

International Preliminary Report on Patentability for PCT/US2008/008539.

Avrahami, I., et al., "Computational studies of resonance wave pumping in compliant tubes", J. Fluid Mech., 2008, vol. 608, pp. 139-160.

Caro, C., et al., "The Mechanics of the Circulation", Cambridge University Press, $2^{nd}$ Edition, 2012, pp. 238-255.

Curtis, S.L., et al., "Reduced systolic wave generation and increased peripheral wave reflection in chronic heart failure", Am J Physiol Heart Circ Physiol, 2007, vol. 293, pp. H557-H562.

Hickerson, A.I., et al., "Experimental study of the behavior of a valveless impedance pump", Experiments in Fkuids, 2005, vol. 38, pp. 534-540.

Hickerson, A.I., et al., "On the resonance of a pliant tube as a mechanism for valveless pumping", J. Fluid Mech., 2006, vol. 555, pp. 141-148.

Kannel, W.B., et al., "Changing epidemiological features of cardiac failure", Br Heart J., 1994, vol. 72, No. 2, Supplement, S3-S9.

Lloyd-Jones, D.M., et al., "Lifetime risk for developing congestive heart failure: the Framingham Heart Study", Circulation, 2002, vol. 106, No. 24, pp. 3068-3072.

Mitchell, G.F., et al., "Pulsatile Hemodynamics in Congestive Heart Failure", Hypertension, 2001, vol. 38, pp. 1433-1439.

Mitchell, G.F., et al., "Arterial stiffness and cardiovascular events: the Framingham Heart Study", Circulation, 2010, vol. 121, No. 4, pp. 505-511.

Moser, M., et al., "Prevention of disease progression, left ventricular hypertrophy and congestive heart failure in hypertension treatment trials", J. Am. Coll. Cardiol., 1996, vol. 27, No. 5, pp. 1214-1218.

Nichols, W.W., et al., "McDonald's Blood Flow in Arteries: Theoretical, Experimental and Clinical Principles, Sixth Edition", CRC Press, 2011, pp. 170-222.

Ooi, H., et al., "Arterial Stiffness and Vascular Load in Heart Failure", Congestive Heart Failure, 2008, vol. 14, No. 1, pp. 31-36.

Pahlevan, N.M., et al., "Aortic Wave Dynamics and Its Influence on Left Ventricular Workload", PLoS ONE, 2011, vol. 6, No. 8, pp. 1-8.

* cited by examiner

CARDIAC ASSIST SYSTEM USING HELICAL ARRANGEMENT OF CONTRACTILE BANDS AND HELICALLY-TWISTING CARDIAC ASSIST DEVICE

PRIORITY CLAIM

The present application is a non-provisional patent application, claiming the benefit of priority of U.S. Provisional Application No. 60/959,297, filed on Jul. 11, 2007, entitled "Method for reinforcing the cardiac pumping function," and U.S. Provisional Application No. 61/010,786, filed on Jan. 11, 2008, entitled "Helically twisting cardiac-apex assist device."

BACKGROUND OF THE INVENTION (1) Field of Invention

The present invention relates to a system and device for assisting cardiac pumping function and, more specifically, to a system and device which assists the cardiac pumping function through a helical arrangement of contractile members.

(2) Description of Related Art

Methods of assisting cardiac pumping function are known in the art. Prior methods have provided assisted contraction transmitted radially or longitudinally around the heart. These motions, however, do not mimic the natural contractile twisting motions of the heart, resulting in inefficient pumping and strain on the heart.

Thus, a continuing need exists for a cardiac assist device which mimics the natural contractile motions of the heart to achieve a more efficient pumping function.

SUMMARY OF INVENTION

The present invention relates to a system and device for assisting cardiac pumping function and, more specifically, to a system and device which assists the cardiac pumping function through a helical arrangement of contractile members.

In one aspect, the present invention teaches a cardiac assist system comprising at least one contractile elastic band configured for helical arrangement around a periphery of a patient's heart, where upon an actuation the at least one contractile band contracts helically, thereby squeezing the heart and assisting the pumping function of the heart.

In another aspect, the system further comprises at least one elastic band arranged in a shape selected from the group consisting of a helix and a double helix.

In yet another aspect of the system of the present invention, the at least one elastic band is comprised of a material selected from the group consisting of biocompatible elastic, viscoelastic materials, active polymers, shape-memory alloys, natural contractile muscle bands, and artificial contractile muscle bands.

In a further aspect, actuation of the system occurs via specific contraction wave propagation.

In another aspect, the system is configured such that the helical contraction is synchronized with the motion of the heart by a pacemaker.

In yet another aspect, the system further comprises a feedback mechanism for adjusting the contraction based on inputs received from the patient's cardiovascular system, the inputs being selected from the group consisting of ventricular pressure, volume, pulse pressure, ECG, volume, and pace maker signal.

In a further embodiment of the system of the present invention, the at least one contractile band is configured to cover up the infarcted and ischemic areas of the heart's epicardial surface, thereby preventing aneurismal remodeling of the heart.

In another embodiment, the present invention comprises a surgical method for attaching at least one contractile muscle tissue elastic band around a patient's heart in a helical arrangement.

Another aspect of the present invention teaches a helically twisting cardiac-apex assist device comprising an open, inverted, substantially conical chamber having an apex, a base, and an elastic chamber wall, the chamber being of a shape and size appropriate for fitting snugly over the apex of a heart. The device further comprises two rotatable ring portions of different diameters, the ring with the larger diameter circumscribing the base of the conical chamber, and the ring with the smaller diameter located near the apex of the chamber. The device further comprises a plurality of substantially helical connecting elements positioned substantially flush with the chamber wall and connecting the two rotatable ring portions, whereby one ring can be twisted relative to the other, causing the helical connecting elements to deform helically, thereby increasing or decreasing a distance between the two rings, and correspondingly increasing or decreasing a volume of the chamber, thereby providing assistance to the pumping functions of the heart.

In yet another aspect the device further comprises an actuator connected with the ring at the apex of the chamber, the actuator configured for anchoring inside a patient's chest cavity, whereby the actuator powers the twisting motion of one ring relative to the other.

In a further aspect of the device of the present invention, the actuator is selected from a group consisting of a twisting rotor and muscle tissue.

In another aspect, the device is configured such that the actuator is synchronized with the motion of the heart by a pacemaker.

In yet another aspect of the device of the present invention, the ring portions and helical connecting portions are comprised of a material selected from the group consisting of shape memory materials and composite materials.

In another aspect, the elastic chamber wall is comprised of a material selected from the group consisting of biocompatible elastic and viscoelastic material.

The present invention also includes a method for surgical implantation of a helically-twisting cardiac-apex assist device with a heart, the method comprising acts of performing a partial, distal bi-ventriculectomy on the heart, and attaching the device with the heart's ventricles.

In another aspect of the method, in the act of performing the partial, distal bi-ventriculectomy, a patient's ventricular septum and papillary muscles are preserved.

In yet another aspect, the surgical method further comprises the act of attaching the device with another body part for support, the other body part being selected from the group consisting of the sternum and the base of the heart.

Finally, the method of the present invention further comprises the act of attaching a patient's papillary muscles and interventricular septum to the device with preservation of their blood supply.

BRIEF DESCRIPTION OF THE DRAWINGS

The objects, features and advantages of the present invention will be apparent from the following detailed descriptions of the various aspects of the invention in conjunction with reference to the following drawings, where.

DETAILED DESCRIPTION

The present invention relates to a system and device for assisting cardiac pumping function and, more specifically, to a system and device which assists the cardiac pumping function through a helical arrangement of contractile members. The following description is presented to enable one of ordinary skill in the art to make and use the invention and to incorporate it in the context of particular applications. Various modifications, as well as a variety of uses in different applications will be readily apparent to those skilled in the art, and the general principles defined herein may be applied to a wide range of embodiments. Thus, the present invention is not intended to be limited to the embodiments presented, but is to be accorded the widest scope consistent with the principles and novel features disclosed herein.

In the following detailed description, numerous specific details are set forth in order to provide a more thorough understanding of the present invention. However, it will be apparent to one skilled in the art that the present invention may be practiced without necessarily being limited to these specific details. In other instances, well-known structures and devices are shown in block diagram form, rather than in detail, in order to avoid obscuring the present invention.

The reader's attention is directed to all papers and documents which are filed concurrently with this specification and which are open to public inspection with this specification, and the contents of all such papers and documents are incorporated herein by reference. All the features disclosed in this specification, (including any accompanying claims, abstract, and drawings) may be replaced by alternative features serving the same, equivalent or similar purpose, unless expressly stated otherwise. Thus, unless expressly stated otherwise, each feature disclosed is only one example of a generic series of equivalent or similar features.

Furthermore, any element in a claim that does not explicitly state "means for" performing a specified function, or "step for" performing a specific function, is not to be interpreted as a "means" or "step" clause as specified in 35 U.S.C. Section 112, Paragraph 6. In particular, the use of "step of" or "act of" in the claims herein is not intended to invoke the provisions of 35 U.S.C. 112, Paragraph 6.

Further, if used, the labels left, right, front, back, top, bottom, forward, reverse, clockwise and counter clockwise have been used for convenience purposes only and are not intended to imply any particular fixed direction. Instead, they are used to reflect relative locations and/or directions between various portions of an object.

(1) Introduction

The present invention relates to a system and device for assisting cardiac pumping function and, more specifically, to a system and device which assists the cardiac pumping function through a helical arrangement of contractile members. The description section below is divided into two parts corresponding to the two main embodiments of the present invention. Section (2) below discloses a cardiac assist system using a helical arrangement of contractile bands and surgical method for implanting the same, while section (3) discloses a helically-twisting cardiac assist device and surgical method for implanting the same.

(2) Cardiac Assist System Using Helical Arrangement of Contractile Bands

Figures 1A, 1B:
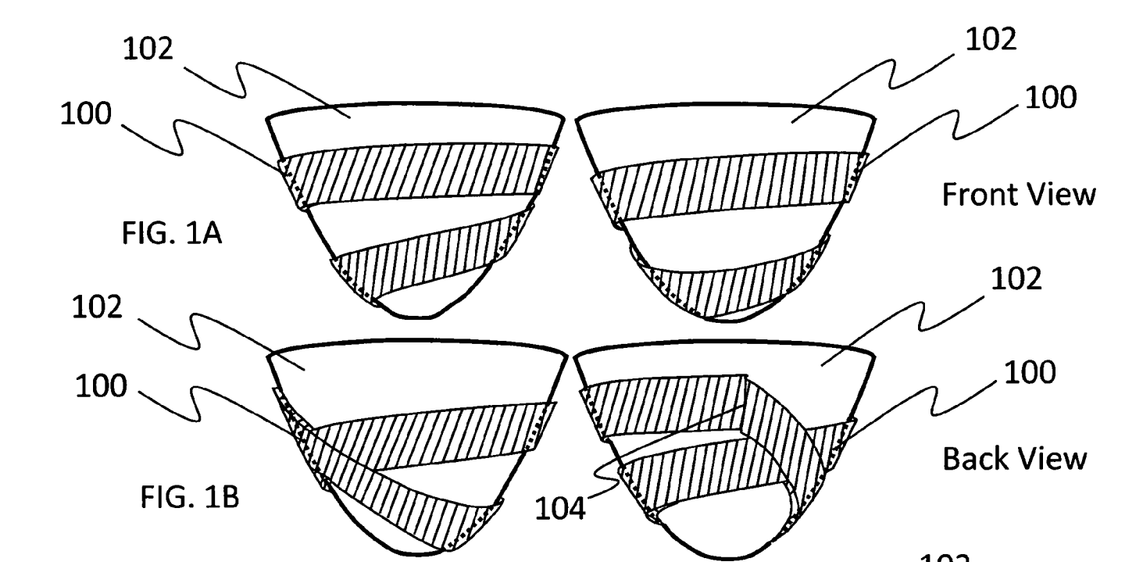
FIG. 1A is a front-view illustration showing two possible arrangements of a contractile band grasping a heart.
FIG. 1B is a back view illustration showing two possible arrangements of a contractile band grasping a heart.
Figure 1C:
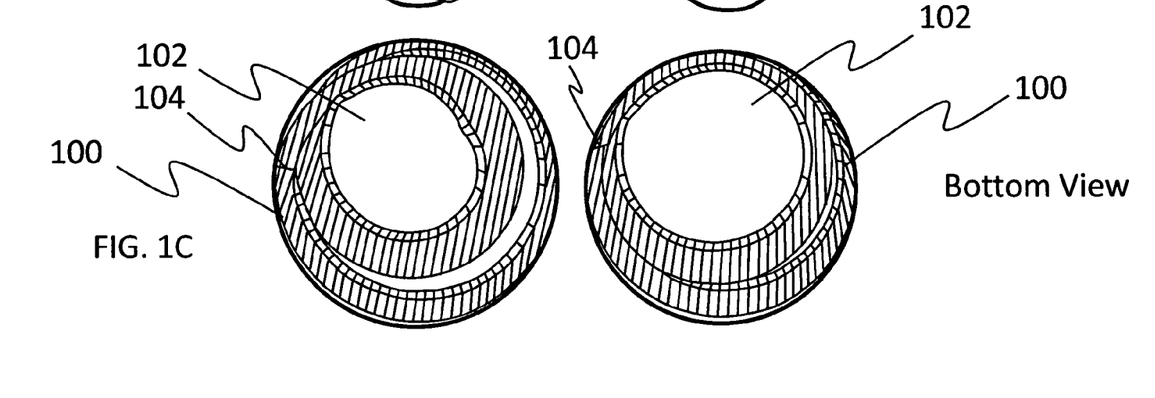
FIG. 1C is a bottom view illustration showing two possible arrangements of a contractile band grasping a heart.

In one aspect, the present invention teaches a cardiac assist system that works based on the contraction of at least one contractile elastic band 100 grasping the heart 102 as shown in FIGS. 1A-C. The contractile band 100 may be arranged in a helix, a double helix, or any other substantially helical arrangement which mimics the natural pumping function of the heart. The arrangements shown in FIGS. 1A-C comprise two possible arrangements of a single contractile band 100 arranged in a double helix around the heart 102, attached to itself at an attachment point 104. The helical band arrangement assists both left and right ventricles during diastole to receive blood from the atria more efficiently, and helps both ventricles to eject the blood more effectively during systole and to improve both local and global cardiac function. The elastic bands 100 can be made of any types of biocompatible elastic or viscoelastic materials such as, but not limited to elastomers like Resilin, silicone rubber, or Polyisobutylen. Other materials suitable for the elastic bands are shape-memory alloys, natural contractile muscle bands, and artificial contractile muscle bands. The bands may also have a framework made of shape-memory materials/fibers.

Figure 2:
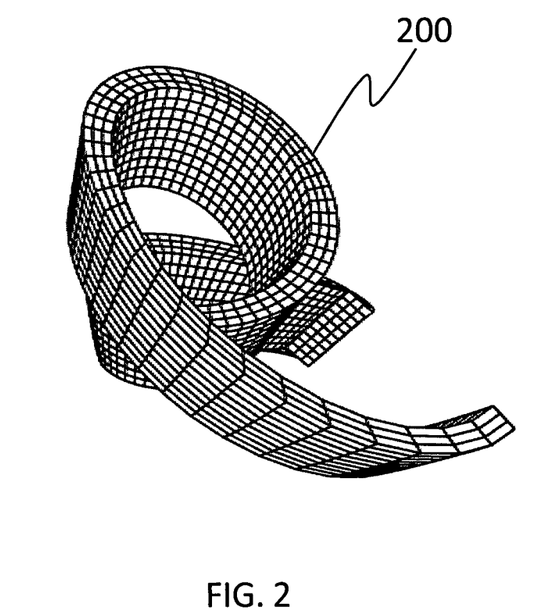
FIG. 2 is an illustration showing the contours of heart myofibril structure independent of the heart.

The system works based on the idea that if contraction waves transmit through the bands at optimal angles around the heart, its pumping efficiency would be higher than if the contraction waves transmit radially or longitudinally. The idea for the system is based on naturally occurring myofibril structure, which can be seen in recent MRI data as detailed in Helm, P., et al., Measuring and Mapping Cardiac Fiber and Laminar Architecture Using Diffusion Tensor MR Imaging. Ann NY Acad Sci, 2005. 1047(1): p. 296-307. Unlike the myoplasty concept this system not only assists the heart globally but also reinforces local function. FIG. 2 is an illustration showing the contours of the myofibril structure 204 independent of the heart.

Another aspect of the cardiac assist system is synchronization of the contraction of the contractile bands with the natural heart motion. Synchronization would be made by devices such as, but not limited to, external and/or internal pacemakers. The activation of the band(s) can mimic the Purkinje activation of the cardiac muscle, i.e. starting at the apex and propagating to the periphery, or follow any other specific contraction wave propagation scheme. This system can also have a feedback mechanism where the contraction waves sent through the bands are adjusted based on inputs received from the heart or vasculature; inputs such as but not limited to blood pressure, volume, ECG, pulse pressure, pace maker signal, etc. As a result the device would be able to self-adjust to changing demands of the heart. In another aspect, the system covers the infarcted/ischemic areas of the epicardial surface of the heart to prevent aneurismal remodeling. The present invention also improves coronary blood flow by accentuating the cardiac motion and pumping function of the heart.

(3) Helically-Twisting Cardiac Assist Device

Figure 3:
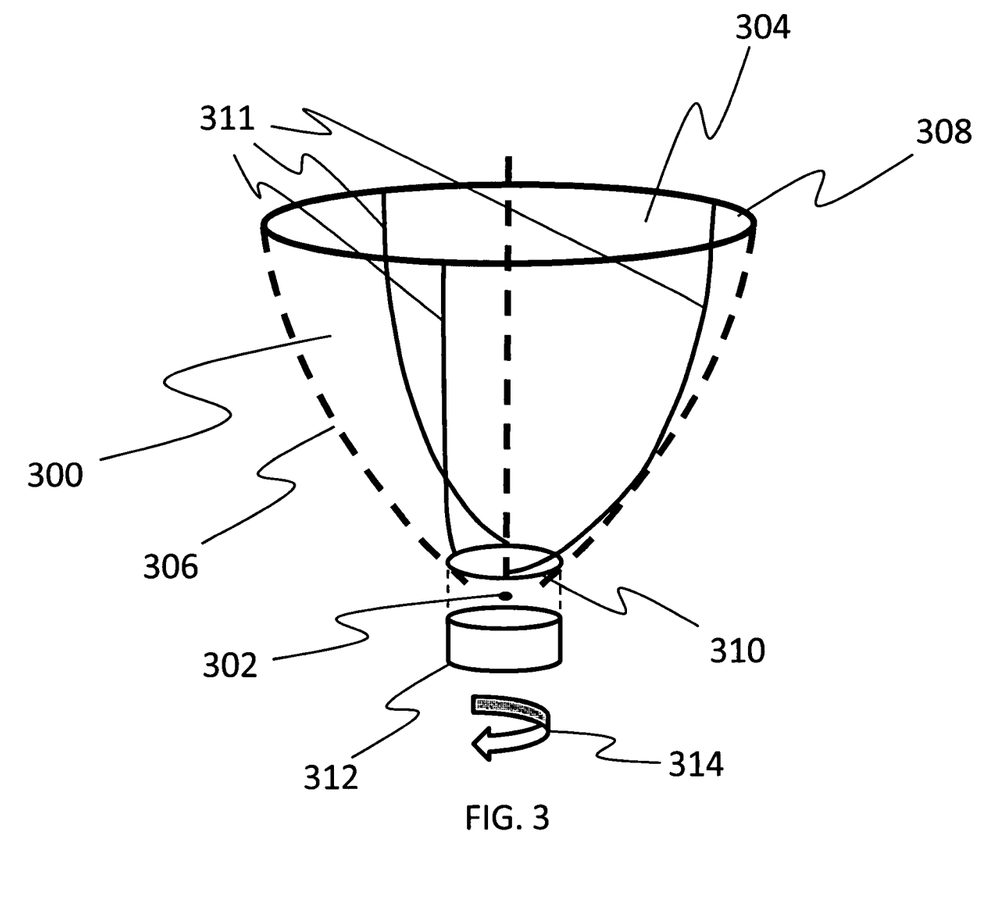
FIG. 3 is an illustration showing the helically-twisting cardiac assist device of the present invention.
Figure 4A:
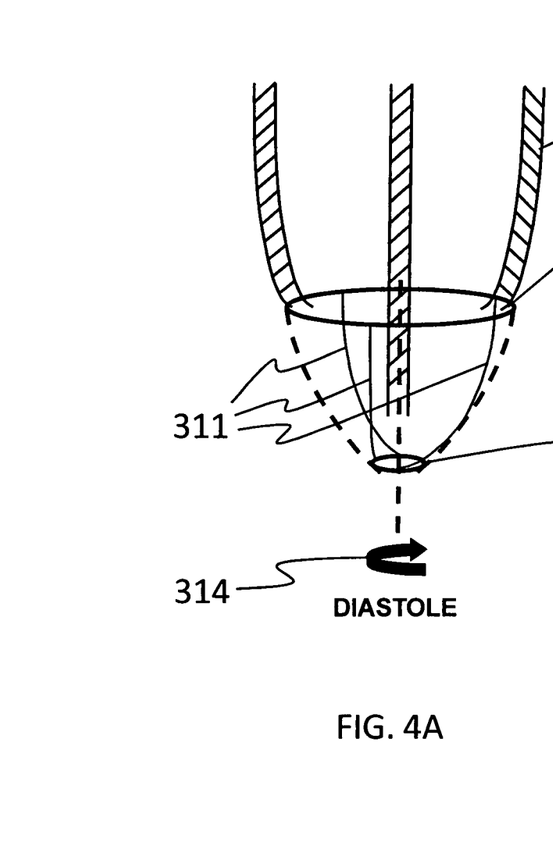
FIG. 4A is an illustration showing the helically-twisting cardiac assist device of the present invention in elongated position and attached with a heart.
Figure 4B:
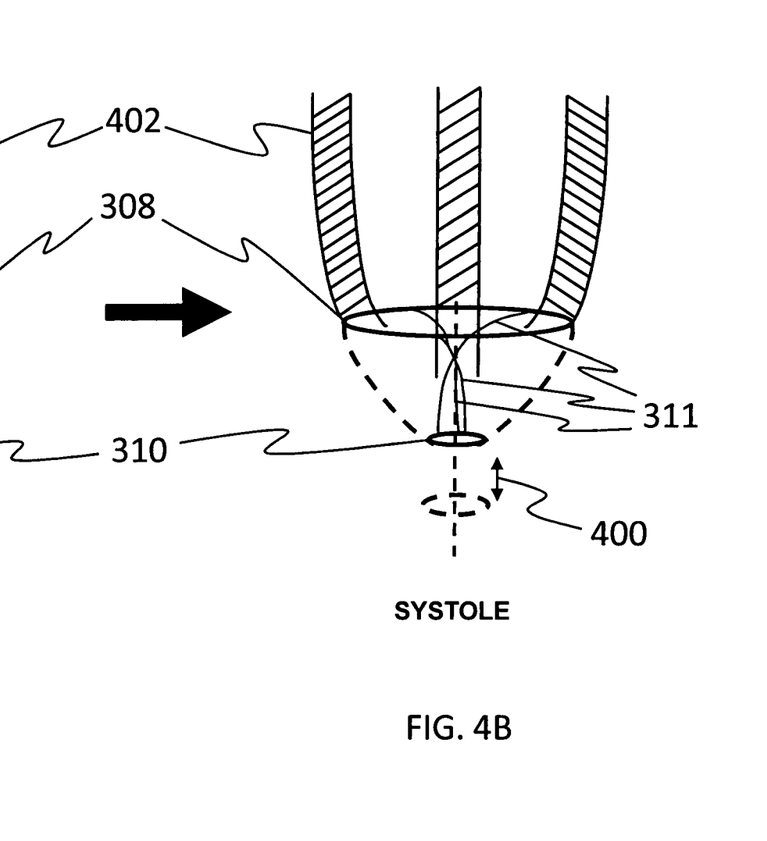
FIG. 4B is an illustration showing the helically-twisting cardiac assist device of the present invention in contracted position and attached with a heart.

In another aspect, the present invention teaches a cardiac assist device that works based on a helically twisting mechanism. The device assists both left and right ventricles during diastole to receive blood from the atria more efficiently, and helps both ventricles to eject the blood more effectively during systole. The shell of the device, as shown in FIG. 3, is an open, inverted, substantially conical chamber 300 having an apex 302, a base 304, and an elastic chamber wall 306, the chamber being of a shape and size appropriate for fitting snugly over the apex of a heart. Inside the conical chamber are two rotatable ring portions of different diameters, the ring with the larger diameter 308 circumscribing the base 304 of the conical chamber 300, and the ring with the smaller diameter 310 located near the apex 302 of the chamber 300. A plurality of substantially helical connecting elements 311 connects the two ring portions 308 and 310 and is substantially flush with the chamber wall 306. The device further comprises an actuator portion 312 connected with the smaller ring 310, where the actuator 312 is configured for anchoring inside a patient's chest cavity. The actuator 312 powers a twisting motion 314 of one ring relative to the other. The actuator 312 can be a motor such as a twisting rotor, which can be attached anywhere inside the chest, or the actuator 312 can be an internal power source such as latissimus dorsi muscle or any other internal structure. Twisting 314 the rings 308 and 310 in opposite relative directions, as shown in FIGS. 4A-B, results in deviation of the helical elements 311 from their original angles, which increases or decreases the distance 400 between two rings. In the case of increasing distance, the chamber induced dilation results in generation of negative pressure during diastole. In contrast, by decreasing the rings' relative distance, the device provides extra pumping force during systole. FIGS. 4A-B also show the device attached with a heart 402. Furthermore, the actuation of the device can be synchronized with the motion of the heart by an external or internal pace-maker.

The rings and helical elements of the device can be made of different selections of shape memory material such as nitinol and/or composite materials. The chamber wall can be made of any type of biocompatible elastic or viscoelastic materials such as, but not limited to, elastomers like Resilin, silicone rubber, Polyisobutylen, etc.

Figure 5A:
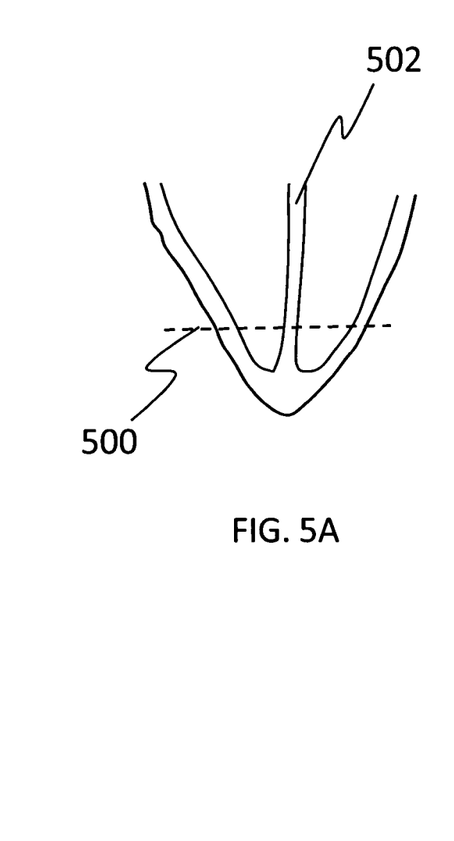
FIG. 5A is an illustration showing a heart with a dotted line indicating the approximate location of the partial, distal bi-ventriculectomy.
Figure 5B:
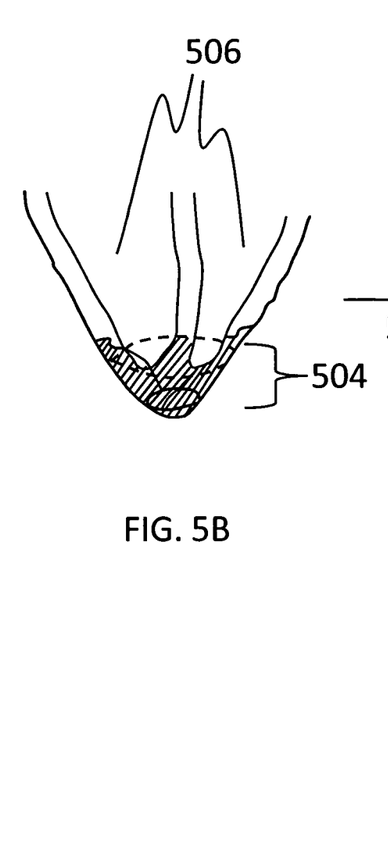
FIG. 5B is an illustration showing the helically-twisting cardiac assist device of the present invention attached with the apex of a heart.
Figure 5C:
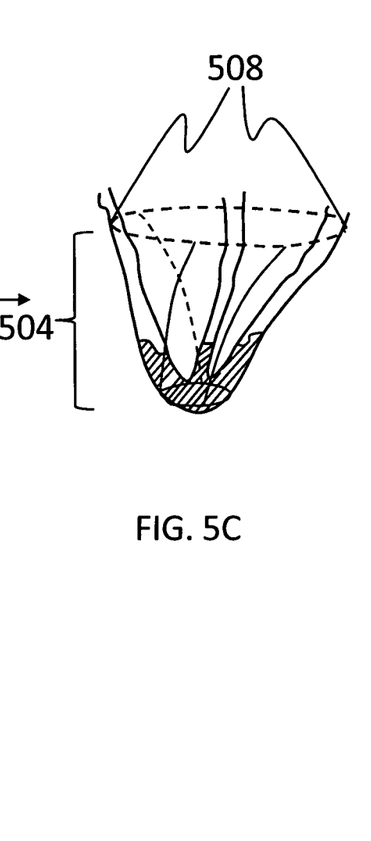
FIG. 5C is an illustration showing the helically-twisting cardiac assist device of the present invention with attachment points to the base of a heart.

The present invention also includes a surgical procedure to implant the device via two or more sequential stages. The first stage, as shown in FIG. 5A, is a partial, distal bi-ventriculectomy 500 with preservation of the anatomical structures such as but not limited to ventricular septum 502 and the papillary muscles. In the second stage, as shown in FIG. 5B, the device 504 is attached to the ventricles 506. The device 504 can be stitched directly to the ventricles 506 and/or supported by additional connections to other internal organs such as but not limited to the sternum or the base of the heart 508. The papillary muscles, interventricular septum 502 and the other structures can be attached to the device 504 with preservation of their blood supply.

What is claimed is:

1. A cardiac assist system comprising:
a single contractile elastic band arranged helically around and encircling a periphery of a patient's heart such that the contractile elastic band does not penetrate the patient's heart,
wherein the contractile elastic band is adapted to contract helically upon actuation with such contraction due to a contractile material property of the band such that the heart is squeezed and the pumping function of the heart is assisted, and
wherein the contractile elastic band comprises only two free ends secured to each other at an attachment point.

2. The system of claim 1, wherein the contractile elastic band is arranged in a shape of a helix or a double helix.

3. The system of claim 1, wherein the contractile elastic band consists essentially of a material selected from biocompatible elastic materials, viscoelastic materials, active polymers, shape-memory alloys, natural contractile muscle bands, and artificial contractile muscle bands.

4. The system of claim 1, wherein the contractile elastic band is adapted to contract helically upon actuation that occurs via specific contraction wave propagation.

5. The system of claim 1, where the contractile elastic band covers up the infarcted and ischemic areas of the heart's epicardial surface, thereby preventing aneurismal remodeling of the heart.

6. The system of claim 1, wherein the contractile elastic band overlaps itself.

7. A surgical method comprising the act of attaching a single contractile elastic band around a patient's heart in a helical arrangement encircling the heart such that the contractile elastic band does not penetrate the heart, wherein only the contractile elastic band is implanted during the surgical procedure, and wherein the contractile elastic band comprises only two free ends secured to each other at an attachment point.

8. The method of claim 7, wherein the contractile elastic band is adapted to contract helically with such contraction due to a contractile material property of the band.

9. The method of claim 8, wherein the contractile elastic band consists essentially of a material selected from biocompatible elastic materials, viscoelastic materials, active polymer, natural contractile muscle bands, shape memory alloys, and artificial contractile muscle bands.

10. The method of claim 7, further comprising overlapping the contractile elastic band with itself.

11. The method of claim 7, wherein the contractile band is adapted to contract helically and assist ventricular ejection of blood during systole.

12. The method of claim 11, wherein attaching the single contractile elastic band around the patient's heart in the helical arrangement encircling the heart is performed such that the contractile elastic band contracts helically and assists ventricular ejection of blood during systole.

13. A cardiac assist system consisting essentially of:
a single contractile elastic band assembly arranged helically around and encircling a periphery of a patient's heart such that the contractile elastic band does not penetrate the patient's heart, wherein the contractile elastic band comprises only two free ends secured to each other at an attachment point, and where upon actuation the contractile band contracts helically with such contraction due to a contractile material property of the band, thereby squeezing the heart and assisting the pumping function of the heart.

14. The system of claim 13, wherein the contractile elastic band overlaps itself.

15. The system of claim 1, wherein the contractile band is adapted to contract helically and assist ventricular ejection of blood during systole.

16. The system of claim 13, wherein the single contractile band is adapted to contract helically and assist ventricular ejection of blood during systole.

* * * * *